(12) United States Patent
Getz et al.

(10) Patent No.: US 6,270,804 B1
(45) Date of Patent: Aug. 7, 2001

(54) SACHET FORMULATIONS

(75) Inventors: John J. Getz, St. Petersburg, FL (US); Steven E. Frisbee, Reston, VA (US); Tushar K. Misra, Leesburg, VA (US); John R. Sisak, Fairfax, VA (US); Pradeepkumar P. Sanghvi, Herndon, VA (US)

(73) Assignee: Biovail Technologies Ltd., Chantilly, VA (US)

( * ) Notice: Subject to any disclaimer, the term of this patent is extended or adjusted under 35 U.S.C. 154(b) by 0 days.

(21) Appl. No.: 09/183,460

(22) Filed: Oct. 30, 1998

Related U.S. Application Data

(60) Provisional application No. 60/080,623, filed on Apr. 3, 1998.

(51) Int. Cl.[7] .............................. A61K 9/16; A61K 9/62; A61K 9/58; A61K 9/20; A61K 9/00
(52) U.S. Cl. .................. 424/490; 424/493; 424/464; 424/465; 424/498; 424/501; 424/494; 424/495; 424/461; 424/462; 424/400
(58) Field of Search ................................ 424/484, 488, 424/489, 490

(56) References Cited

U.S. PATENT DOCUMENTS

| 5,429,836 | 7/1995 | Fuisz | 426/601 |
|---|---|---|---|
| 5,458,823 | 10/1995 | Perkins et al. | 264/8 |
| 5,587,172 | 12/1996 | Cherukuri et al. | 424/401 |
| 5,597,416 | 1/1997 | Fuisz et al. | 127/30 |
| 5,683,720 | 11/1997 | Myers et al. | 424/489 |
| 5,840,334 | * 11/1998 | Raiden et al. | 424/464 |
| 5,869,098 | * 2/1999 | Misra et al. | 424/484 |

FOREIGN PATENT DOCUMENTS

| WO 88/06558 | 9/1988 | (WO) | B65D/83/04 |
|---|---|---|---|
| WO 95/34290 | 12/1995 | (WO) | A61K/9/14 |
| WO 95/34293 | 12/1995 | (WO) | A61K/9/20 |

\* cited by examiner

Primary Examiner—Thurman K. Page
Assistant Examiner—Isis Ghali
(74) Attorney, Agent, or Firm—Pillsbury Winthrop LLP

(57) ABSTRACT

Bioaffecting sachets, or powders, containing coated liqui-flash microspheres and partially recrystallized shearform floss particles are disclosed. The sachets give organoleptically acceptable properties, including a pleasing mouthfeel, when orally ingested.

20 Claims, No Drawings

SACHET FORMULATIONS

This application claims the benefit of U.S. provisional application Ser. No. 60/080,623, filed Apr. 3, 1998.

FIELD OF THE INVENTION

The compositions of the invention are sachets, that is free flowing powders, containing combinations of coated bioaffecting microspheres and shearform floss particles. When ingested, the combinations become somewhat syrupy in the mouth, giving a pleasing mouthfeel and enhanced organoleptic acceptability.

RELATED APPLICATIONS

U.S. Ser. No. 08/642,027, filed Apr. 29, 1996, discloses the use of drug-containing microspheres in orally ingestible powder delivery systems. These systems do not contain the floss component described herein.

U.S. Ser. No. 08/642,026, also filed Apr. 29, 1996, discloses the preparation of compressed tablets from compositions containing the drug-containing microspheres of the above-referenced application.

In U.S. Ser. No. 08/915,068, filed Aug. 20, 1997, tablets from compositions containing liquiflash microspheres and shearform floss particles are discussed. Xylitol is a preferred floss constituent. The compressed tablets in this application do not have the organoleptic properties of the sachets described herein.

U.S. Ser. No. 08/874,215, filed Jun. 13, 1997, describes the preparation of microspheres which may contain bio-affecting agents using customized spinning devices.

U.S. Ser. No. 08/854,344, filed May 12, 1997, covers the use of certain thermoforming techniques to produce shearform flosses, also called shearform matrices.

The above applications, all of which are assigned to Applicants' assignee, Fuisz Technologies Ltd, are incorporated herein by reference.

BACKGROUND OF THE INVENTION

Microspheres and flosses have been used individually in a variety of products. They have also been used together to make compressed dosage forms, such as tablets.

Liquiflash microspheres are the subject of U.S. Pat. No. 5,683,720, incorporated herein by reference. The microspheres have enhanced flowability, making them easy to coat, process, and store.

PCT Publication WO 88/06558, published Sep. 7, 1998, deals with powder dosage forms containing coated pellets of bio-affecting agents. These powders do not contain a floss component.

Shearform flosses have been used in a variety of food and pharmaceutical applications, such as the following:

U.S. Pat. No. 5,429,836, incorporated herein by reference, describes the flash flow process and its use to make amorphous solid shearform matrices having flake-like form.

U.S. Pat. No. 5,587,172, also incorporated herein by reference, discusses the use of flash heat techniques to make sucrose-containing flosses, which are used to make tablets.

The use of shearform matrices to make compacted comestible units is described in co-assigned PCT application No. PCT/US95/07144, filed Jun. 6, 1995. The PCT case discloses: (1) providing a partially recrystallized shearform matrix; (2) combining the matrix with additives to form flowable, compactable blends; and (3) compacting the blends to form comestible units, such as tablets.

Additionally, PCT publication WO 95/34293 (published Dec. 21, 1995) from co-assigned PCT Application No. PCT/US95/07194, filed Jun. 6, 1995, discloses a process for making rapidly dissolving dosage units. In this PCT application, a shearform matrix is combined with an additive, and the combination is molded to make a unit dosage form. Tamping may be used to compact the dosage form and increase its integrity.

SUMMARY OF THE INVENTION

The invention provides bio-affecting sachet formulations containing organoleptically acceptable combinations of bio-affecting spherical microparticles and shearform flosses, as well as methods of making the formulations.

Applicants have discovered that the combinations described herein yield pleasant-tasting, organoleptically acceptable sachet, or powder, formulations suitable for use as dosage forms for delivering bio-affecting agents.

The sachets combine the desirable disintegration properties of partially crystalline flosses with the enhanced processability of microspheres. When mixed with excipients, the microsphere/floss combinations are solid, free-flowing consumer-ready products that can be packaged as is. When ingested, they become syrupy in the mouth and give a pleasant mouthfeel.

The sachets require no special shaping or molding operations. Thus, the compaction, compression or tamping steps used with other dosage forms are not needed.

DETAILED DESCRIPTION OF THE INVENTION

Unless otherwise stated, the parts and percentages used in the specification are weight percentages, based upon total composition weight. The terms "matrix" and "floss" are used interchangeably.

The sachet formulations of the invention are solid powders containing three essential components:

(A) coated spherical microparticles containing one or more bioaffecting agents;

(B) partially recrystallized shearform floss particles produced from compositions containing at least one saccharide-based carrier and one sugar alcohol; and (C) one or more additives selected from the group consisting of: lubricants, flavors, flavor enhancers, glidants, fillers, colorants and perfumes.

Coated Microspheres

The bio-affecting agents are used in the form of coated microparticles of generally spherical shape. While they are preferably coated liquiflash microspheres, they can be spherical particles of bio-affecting agents coated or encapsulated with taste-masking or other coatings (e.g., DESCOTE particles).

Suitable liquiflash microspheres and other spheroidal particles have mean diameters of 0.1 to 600 microns, preferably 200 microns or less. The liquiflash particles can be made by "liquiflash" processes, such as those disclosed in U.S. Pat. No. 5,683,720, incorporated herein by reference.

"Liquiflash" processing involves the use of heat and pressure to reduce the feedstock to a condition in which resistance to flow, e.g., viscosity, which impedes the propensity to form liquid droplets, is eliminated. In this condition, the mass has become liquid or "liquiform". Once all resistance to flow is gone, shear force is applied to the feedstock until discrete particles separate from the mass. The particles, called "liquiflash" particles, have a size and shape influenced only by natural mass separation of the flowing feedstock. U.S. Pat. Nos. 5,458,823 and 5,683,720, both incorporated herein by reference, show processes and devices used for such processing.

One useful process for making microspheres is exemplified by the production of ibuprofen spheres set out below. However, any other method of producing suitable spherical particles containing bio-affecting agents can be employed.

The microspheres of the invention include one or more bio-affecting agents, also called active ingredients. These are typically prescription or over the counter medications.

The bio-affecting agents used may be selected from a broad range of drug, therapeutic or prophylactic materials. Respective classes include those in the following therapeutic categories: ace-inhibitors; alkaloids; antacids; analgesics; anabolic agents; anti-anginal drugs; anti-allergy agents; antiarrhythmia agents; antiasthmatics; antibiotics; anticholesterolemics; anticonvulsants; anticoagulants; antidepressants; antidiarrheal preparations; antiemetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; antiulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents and others.

Active agents which may be used in the invention include: acetaminophen (APAP); acetic acid; acetylsalicylic acid (i.e. aspirin), including its buffered forms; acrivastine; albuterol and its sulfate; alcohol; alkaline phosphatase; allantoin; aloe; aluminum acetate, carbonate, chlorhydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; brompheniramine and its maleate; buspirone; caffeine; calamine; calcium carbonate, casinate and hydroxide; camphor; captopril; cascara sagrada; castor oil; cefaclor; cefadroxil; cephalexin; centrizine and its hydrochloride; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine and its hydrochloride; cinnamedrine hydrochloride; citalopram; citric acid; clarithromycin; clemastine and its fumarate; clonidine and its hydrochloride salt; clorfibrate; cocoa butter; cod liver oil; codeine and its fumarate and phosphate; cortisone acetate; ciprofloxacin hydrochloride; cyanocobalamin; cyclizine hydrochloride; cyproheptadine and its hydrochloride; danthron; dexbromopheniramine maleate; dextromethorphan and its hydrohalides; diazepam; dibucaine; dichloralphenazone; diclofen and its alkali metal salts; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fluoxetine; folic acid; fosphenytoin; 5-fluorouracil (5-FU); fluoxetine and its hydrochloride; furosemide; gabapentan; gentamicin; gemfibrozil; glipizide; glycerine; glyceryl stearate; granisetron and its hydrochloride; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen (IBP); indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loratadine; lovastatin; luteinizing hormore; LHRH (lutenizing hormone replacement hormone); magnesium carbonate, hydroxide, salicylate, and trisilicate; meclizine and its hydrochloride; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole and its hydrochloride; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine and its hydrochloride salt; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine;

sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Mixtures and pharmaceutically acceptable salts of these and other actives can be used.

Particularly useful active agents are analgesics, including non-steroidal anti-inflammatory drugs (NSAIDs) and anticholesterolemics.

Analgesics include aspirin, acetaminophen, acetaminophen plus caffeine, and non-steroidal anti-inflammatory drugs (NSAIDs).

Useful NSAIDs include ibuprofen; diclofenac and its alkali metal salts; fenoprofen and its metal salts; ketoprofen, naproxen and its alkali metal salts; nimesulide; and piroxicam and its salts. Ibuprofen and nimesulide are preferred NSAIDs.

Among the anticholesterolemics, the statins, e.g., lovastatin, provastatin and the like are notable. Combinations which include niacin are also useful.

Combinations of various types of drugs, as well as combinations of individual drugs, are contemplated.

In some preferred embodiments, the bio-affecting agent is combined with spheronization aids and/or solubilizers before flosses are formed. Useful spheronization aids include carnauba wax, fatty acid esters and other lipophilic materials.

Useful solubilizers include surfactants, such as the polyethylene oxide/polypropylene oxide surfactants known as "Pluronics". Pluronic F68 is preferred.

The microspheres are coated or encapsulated, to coating levels of about 10% to about 50%, with taste-masking or controlled release coating materials using conventional coating devices, e.g., using fluidized beds and the like.

Suitable coatings include mono- and di-glycerides, as well as polymeric materials, such as ethylcellulose (EC), methylcellulose, hydroxypropylcellulose (HPC), hydroxypropylmethylcellulose (HPMC) and the like. Commercial coating products sold as Eudragit NE30D, Eudragit R S, Eudragit R L, Eudragit S, Klucel E F or combinations thereof are useful. One preferred coating contains a 1:1 ethylcellulose/hydroxypropylcellulose blend at a 30% coating level.

DESCOTE particles, supplied by Particle Dynamics of St. Louis, Mo., are among the other suitable coated microparticles useful herein. DESCOTE particles can contain a variety of bio-affecting agents including vitamin C and the like. They are generally coated or encapsulated with mono- or diglycerides or other taste-masking substances.

Shearform Flosses

The sachet formulations of the invention are based on flosses made from feedstocks which comprise a saccharide and a sugar alcohol.

It is believed, for reasons set out below, that the content of xylitol in the feedstock should be kept at a minimum, with contents of 15% or less, preferably 10% or less, and most preferably 5% or less being operable. Xylitol-free flosses are highly preferred.

Unlike the flosses disclosed in U.S. Ser. No. 08/915,068, the flosses used herein contain minimal amounts of xylitol.

It has been found that the presence of more than 15% xylitol tends to make the floss particles too sticky, so that they agglomerate or clump together and do not form free-flowing sachets. One preferred floss is produced from a composition consisting of 89.75% sucrose, 10% sorbitol, and 0.25% Polysorbate 80 (Tween 80).

Active agents and other conventional food or pharmaceutical ingredients can be added, in suitable amounts, to the self-binding shearform matrices of the present invention during the production of the flosses and/or after the flosses are collected and reduced in size.

The preparation of flosses suitable for use in the present invention is disclosed in co-assigned patent applications PCT application No. PCT/US95/07144, filed Jun. 6, 1995 and PCT publication WO 95/34293, both incorporated herein by reference. Preferably, the floss is a "shearform matrix" produced by subjecting a feedstock which contains a sugar carrier to flash-heat processing.

In the flash-heat process, the feedstock is simultaneously subjected to centrifugal force and to a temperature gradient which raises the temperature of the mass to create an internal flow condition which permits part of it to move with respect to the rest of the mass. The flowing mass exits through openings provided in the perimeter of a spinning head. The temperature gradient is supplied using heaters or other means which cause the mass' temperature to rise. Centrifugal force in the spinning head flings the internally flowing mass outwardly, so that it reforms as discrete fibers with changed structures.

An apparatus which produces suitable conditions is a modified floss making machine, such as that described in a U.S. application Ser No. 08/854,344, filed on May 12, 1997. The content of that application is hereby incorporated by reference.

Typically, spinning is conducted at temperatures and speeds of about 180 to 250 degrees C. and 3,000 to 4,000 rpm, respectively.

Suitable spinner heads include that disclosed in U.S. Pat. No. 5,458,823, assigned to Applicants' assignee, which is hereby incorporated by reference.

Other useful apparatuses or processes which provide similar forces and temperature gradient conditions can be used. Extrusion is contemplated.

The flosses used herein include a carrier, or feedstock, material which carrier material comprises at least one selected from materials which are capable of undergoing the physical and/or chemical changes associated with flash heat processing. Useful carriers include carbohydrates which become free-form particulates when flash heat processed. Saccharide-based carriers, including saccharides (i.e., sugars), polysaccharides and mixtures thereof can be used.

The feedstocks used in the invention can include carriers chosen from various classes of "sugars". "Sugars" are those substances which are based on simple crystalline mono- and di-saccharide structures, i.e., based on $C_5$ and $C_6$ sugar structures. They may include glucose, sucrose, fructose, lactose, maltose, pentose, arbinose, xylose, ribose, mannose, galactose, sorbose, dextrose and sugar alcohols preferably excluding xylitol, such as sorbitol, mannitol, maltitol, isomalt, sucralose and the like and mixtures thereof. Sucrose is the preferred sugar. Xylitol should not be used in the feedstock.

The flosses may be rendered partially or completely crystalline by one or more of the following crystallizing techniques, several of which use crystallization-promoting ingredients, termed "crystallization enhancers" and "crystallization modifiers". The nature of the matrix feedstock determines whether the matrix is recrystallized after it is formed. Nonetheless, the terms "crystallization" and "recrystallization" are used interchangeably in the following discussion.

One technique for recrystallizing involves the use of crystallization enhancers. These enhancers are crystallization promoting additives used after the floss has been formed. Suitable crystallization enhancers include ethanol, polyvinylpyrrolidone, water (e.g. moisture), glycerine, radiant energy (e.g., microwaves) and the like. Combinations can be used. When they are physical materials, typical amounts of these enhancers range from about 0.01% to about 10.0% by weight, preferably about 1% to about 5% of the total floss weight. The use of about 2% to about 4% ethanol is highly preferred.

Another technique relates to the use of crystallization modifiers. These crystallization modifiers are floss ingredients, used at levels of about 0.01% to about 20.0% by weight of the floss.

Surfactants are preferred crystallization modifiers. Other materials which are non-saccharide hydrophilic organic materials may also be used. Useful modifiers preferably have a hydrophilic to lipid balance (HLB) of about 6 or more. Such materials include, without limitation, anionic, cationic, and zwitterionic surfactants as well as neutral materials with suitable HLB values. Hydrophilic materials having polyethylene oxide linkages are effective. Those with molecular weights of at least about 200, preferably at least 400, are highly useful.

Crystallization modifiers useful herein include: lecithin, polyethylene glycol (PEG), propylene glycol (PPG), dextrose, the SPANS and TWEENS (Polysorbates) which are commercially available from ICI America, and the surface active agents known as "Carbowax". Generally, the polyoxyethylene sorbitan fatty acid esters kown as POLYSORBATES or TWEENS, or combinations of such modifiers, are used. Crystallization modifiers are usually incorporated into flosses in amounts between about 0% and 10%.

Optionally, the flosses are allowed to recrystallize, with or without added ingredients to promote crystallization, either before or after they are combined with the non-matrix component(s), bio-affecting agents or other additives. Typically, the recrystallization level reaches at least about 10%. U.S. Pat. No. 5,597,416 describes a process for recrystallizing in the presence of additives.

Methods for effecting the recrystallization of the flosses include: use of Polysorbate 80 (Tween 80) or other crystallization modifier(s) in the matrix feedstock; aging of the matrix for up to several weeks, contacting the matrix with sufficient moisture and heat to induce crystallization, and treating the floss or the floss-containing composition with ethanol or another crystallization enhancer. Combinations of these may be used.

When ethanol is used as a crystallization enhancer, it is used in amounts, based upon the weight of the matrix, of about 0.1% to about 10%, with amounts of about 2.0% to about 4.0% being very effective. The preformed matrix is contacted with liquid ethanol. Excess ethanol is evaporated by drying. The drying step is carried out using vacuum, intermittent rotation of the mixing blades (ploughs), tray drying, heating in a jacketed mixer or combinations of these techniques.

Following treatment using one or more of these techniques, the matrix becomes partially recrystallized on standing for a period ranging from about a few minutes up to several weeks. When the floss is about 10 to about 30% recrystallized, it is ready for blending with other ingredients.

Recrystallization of the matrix can be monitored by measuring the transmittance of polarized light therethrough or by the use of a scanning electron microscope. Amorphous floss or shearform matrix does not transmit polarized light and appears black in the light microscope when viewed with polarized light. Using bright field microscopy or the scanning electron microscope, the surface of the floss appears very smooth. In this condition, it is 0% recrystallized. That is, the floss is 100% amorphous.

Recrystallization of amorphous matrix starts at the surface of the mass and can be modified, e.g., accelerated, by the presence of crystallization modifiers, as well as moisture. Initiation of recrystallization is evidenced by a birefringence observed on the surface of the shearform matrix (floss) as viewed with polarized light. There are faint points of light riddled throughout the matrix' surface. When birefringence appears, recrystallization is between about 1% and 5%.

As recrystallization proceeds, the birefringence on the surface of the matrix grows continually stronger and appears brighter. The points of light grow in size, number and intensity, seeming to almost connect. Using bright field or scanning electron microscopy, the surface of the matrix appears wrinkled. At this point, about 5 to 10% recrystallization has occurred.

Surfactant (e.g., Tween 80) droplets become entrapped within the matrix. These droplets are obscured as recrystallization proceeds. As long as they are visible, the floss is generally not more than about 10% to 20% recrystallized. When they are no longer observable, the extent of recrystallization is about 20% about 50%.

The recrystallization of the matrix results in reduction of the total volume of material. Since recrystallization begins at the surface of the floss, a crust is formed which maintains the size and shape of the floss. There is an increase in the total free volume space within the floss as recrystallization nears completion, which manifests itself as a void inside the floss. This is evidenced by a darkened central cavity in light microscopy and a hollow interior in scanning electron microscopy. At this stage, the floss is believed to be about 50% to about 75% recrystallized.

The final observable event in the recrystallization of floss is the appearance of fine, "cat whisker-like" needles and tiny blades which grow and project from the surface of the floss. These fine crystals, believed to be indicative of the presence of one or more sugar alcohol(s), literally cover the floss like a blanket of fuzz. These features can be easily recognized by both light and electron microscopes. Their appearance indicates the final stage of recrystallization. The floss is now 100% recrystallized, i.e., substantially non-amorphous.

Following flash-heat or other processing to produce the floss, the strands of the floss are reduced in size, i.e., granulated, macerated or chopped, into particles useful for further processing. Useful particles of floss generally pass through a #20 mesh screen.

Microsphere/Floss Combinations

The combination of microspheres and floss generally contain about 20% to about 80% partially recrystallized floss. The quantities of other sachet ingredients, ie., additives, may vary widely.

The sachet formulations can contain conventional additives. These additives may be incorporated into the flosses or they may be mixed with preformed flosses. Useful amounts of conventional additives range from about 0.01% to about 80% by weight, based on the weight of the sachets formulations. The quantities may vary from these amounts, depending on the functions of the additives and the characteristics desired in the Other additives which may be included are lubricants, colorants, flow agents, glidants, fillers, perfumes, flavors, flavor enhancers, such as sweeteners (both artificial and natural), and other conventional pharmaceutical additives, e.g., effervescent agents.

Conventional additives may be selected from a wide variety of materials such as lubricants, glidants, anti-caking agents and flow agents. For example, lubricants such as adipic acid, magnesium stearate, calcium stearate, zinc stearate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil and the like may be employed, with sodium stearyl fumarate preferred. Waxy fatty acid esters, such as glyceryl behenate, sold as "Compritol" products, can be used. Other useful commercial lubricants include "Stear-O-Wet" and "Myvatex TL". Mixtures are operable.

Lubricants are used in amounts ranging from about 0% to about 10%, with about 0.01% to about 5.0% typically used.

Glidants such as starch, talc, lactose, stearates, dibasic calcium phosphate, magnesium carbonate, magnesium oxide, calcium silicate, Cabosil, Syloid, and silicon dioxide aerogels may be employed.

Glidants are present in amounts ranging from about 0% to about 20%, with amounts of about 0.1% to about 5.0% being typical. Lactose, which may be a glidant or filler, can be added to the chopped floss at about 2% concentration to inhibit clumping.

For example, fillers may be used to increase the bulk of the sachet. Some of the commonly used fillers are calcium sulfate, both di- and tri-basic; starch; calcium carbonate; microcrystalline cellulose; modified starches, lactose, sucrose; mannitol and sorbitol.

Flavors may be chosen from natural and synthetic flavoring liquids. An illustrative list of such agents includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such a lemon, orange, grape, lime and grapefruit an fruit essences, including apple, pear, peach, grape, strawberry, raspberry, cherry, plum, pineapple, apricot, or other fruit flavors.

Other useful flavorings include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodedenal (citrus, mandarin); mixtures thereof and the like.

The sweeteners may be chosen from the following non-limiting list: glucose (corn syrup), dextrose, invert sugar, fructose, and mixtures thereof (when not used as a carrier); saccharin and its various salts, such as the sodium salt; dipeptide sweeteners such as aspartame; dihydro-chalcone compounds, glycyrrhizin; *Stevia Rebaudiana* (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-one-2,2-dioxide, particularly the potassium salt (acesulfame-K), and sodium and calcium salts thereof. Other sweeteners may also be used.

Some embodiments include effervescent agents to aid in masking the objectional taste of active ingredients, such as vitamins, medicines and/or minerals, etc. The positive organoleptic sensation achieved by the effervescent action in the mouth, as well as the texture, speed and sensation of disintegration, aid in masking undesirable flavor notes.

Color additives can be used. Such color additives include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

In one embodiment, the bio-affecting agent is blended with suitable spheronization aids and/or solubilizers and processed into liquiflash microspheres. These microspheres are then coated with one or more taste-making and/or controlled release coatings.

The following examples illustrate the invention.

EXAMPLE I

Ibuprofen Sachet Formulation

A sachet (C) was prepared using ibuprofen spheres (A) and a sucrose/sorbitol floss (B).

(A) Ibuprofen Spheres Component

Ibuprofen was processed into spheres as follows:

An ibuprofen powder feedstock was fed to a 5-inch spinning head disclosed in a U.S. Ser. No. 08/874,215, filed on Jun. 13, 1997. The head was rotated at about 3600 rpm while the heating elements were raised to a temperature which produced the liquiflash conditions. The feedstock also contained 10% Compritol 888 ATO and 2% Gelucire 50/13. (Compritol 888 ATO is glycerol behenate NF, a lipophilic additive from Gattefosse S. A., a French company. Gelucire, a polyethylene glycol 32 glyceryl ester solubility enhancer, is also available from Gattefosse.)

After exiting the spinning head, the material was permitted to free fall a distance of from 6 to 8 feet below the head. The product consists of spheres having a highly consistent particle size, with mean particle diameters ranging from about 180 to about 200 microns.

The spheres were coated, using a Glatt fluidized head coater, with a composition containing 34.5% Eudiogit NE30D, 11.5% hydroxypropyl methylcellulose, 50% talc and 4% adipic acid to a 12% coating level.

(B) Floss Component

A floss was made from the ingredients listed below using the following procedure:

All ingredients were placed in a mixer and blended well. The blended mix was spun into floss in the device taught in U.S. Ser. No. 08/854,344, filed May 12, 1997, at 60 Hz at about 230 to 250 degrees C.

| Sucrose | 89.75% |
|---|---|
| Sorbitol | 10.0% |
| Tween 80 | 0.25% |

The floss was placed in a Littleford FM mixer/granulator and chopped for 30 seconds. The chopped floss was then granulated by spraying 2% ethanol thereon, with intermittent rotation of the choppers for a total of 5 minutes, until 30 g. of ethanol was added. When all of the ethanol had been added, the mixer jacket was heated to 105 degrees F. The exhaust pump was turned on. The plows were rotated intermittently for 10 seconds every 2 minutes for 30 minutes.

EXAMPLE II

Another Sucrose/Sorbitol Floss

The floss was prepared from a mixture of 89.75% sucrose, 10% sorbitol, and 0.25 parts of TWEEN 80. The mix was flash flow processed in a device described in U.S. Ser. No. 08/854,344. Two kilograms of this material was spun under ambient conditions of 60° F. and 35% relative humidity. Spinning was conducted at 3600 rpm (60 Hz). The spun floss was collected and chopped in a Littleford mixer for about 10 minutes.

Following chopping, the floss was partially recrystallized by contacting it with 4% ethanol. Using warming and vacuum, the mixer blades were then rotated in 10 second intervals to drive off excess ethanol. The finished floss was granular and free flowing.

EXAMPLE III
Other Flosses

Using procedures described in Example II, flosses were made from the following:

| (1) | Sucrose | 74.75% |
|---|---|---|
|  | Mannitol | 25% |
|  | Tween 80 | 0.25% |
| (2) | Sucrose | 71.75% |
|  | Mannitol | 25% |
|  | Lactose | 3% |
|  | Tween 80 | 0.25% |
| (3) | Sucrose | 79.75% |
|  | Sorbitol | 10% |
|  | Xylitol | 10% |
|  | Tween 80 | 0.25% |
| (4) | Sucrose | 76.75% |
|  | Sorbitol | 10% |
|  | Xylitol | 10% |
|  | Lactose | 3% |
|  | Tween 80 | 0.25% |
| (5) | Sucrose | 71.75% |
|  | Sorbitol | 15% |
|  | Xylitol | 10% |
|  | Lactose | 3% |
|  | Tween 80 | 0.25% |
| (6) | Sucrose | 71.75% |
|  | Sorbitol | 15% |
|  | Tween 80 | 0.25% |

Examples IV and V show the preparation of acetaminophen sachets.

EXAMPLE IV
Acetaminophen Sachet

Using a procedure similar to that described in Example I, acetaminophen (APAP) microspheres were made from a mix of 90% APAP, 7.5% carnauba wax and 2.5% Pluronic F68 (also called "Poloxamer 188" and "Lutrol F68").

The Pluronic F68 was milled through a Fitz mill using a 40 mesh screen. The three ingredients were blended in a Littleford FKM600 mixer at 60 Hz plow speed with choppers on for 10 minutes. The blend was spun using the 5-inch spinning head disclosed in U.S. Ser. No. 08/874,215, filed Jun. 13, 1997, at 60 Hz and 37% power. The microspheres were collected and sieved. The microspheres that passed through 40 mesh and were retrieved on 120 mesh were used.

They were coated at 25% coating level with a 45:55 ethyl cellulose/hydroxypropyl propyl cellulose taste masking blend. The floss was made, using the procedure of Example II, from the following ingredients:

| Sucrose | 74.75% |
|---|---|
| Mannitol | 25.0% |
| Polysorbate 80 | 0.25% |

The floss was chopped in a Littleford mixer with 2% lactose and treated with ethanol (4% based on floss weight).

It was then dried at 45° C. for 90 minutes and milled/sieved through a 20 mesh screen.

The sachet formulation contained these ingredients:

| Taste-masked acetaminophen microspheres | 25.6% |
|---|---|
| Floss particles | 72.7% |
| Aspartame powder | 0.7% |
| Syloid | 0.5% |
| Grape flavor | 0.5% |

The ingredients were combined as follows:

Half of the floss and all of the spheres were layered on the other half of the floss in a 5 quart PK blender. They were then blended for about 3 minutes. The aspartame, flavorant and Syloid were then added and mixed for an additional 3 minutes. The contents of the blender was removed and passed through a #20 mesh screen. 500 mg fill weight samples containing 80 mg APAP were sealed in foil sachet packages.

EXAMPLE V
Acetaminophen Sachet

Using procedures similar to those of Example IV, another sachet was containing from the following:

| Coated APAP microspheres* | 50.98% |
|---|---|
| Lemon flavor | 1.5% |
| Citric Acid | 2% |
| Mannitol | 5% |
| Xylitol | 5% |
| Xanthan gum | 1% |
| Silicon dioxide | 0.5% |
| Aspartame | 0.1% |
| Magnasweet | 0.05% |
| Floss of Example IV | 33.87% |

*The spheres contained 85% APAP, 7.5% carnauba wax and 7.5% Pluronic F68. They were coated with a 1:1 ethyl cellulose(EC)/hydroxypropylcellulose (HPC) blend at 30% coating level.

EXAMPLE VI
Aspirin Sachet

Microspheres were produced from the following composition using a spinning procedure and device similar to those in Example I. The microsphere composition contained:

| Milled aspirin | 80% |
|---|---|
| Carnauba wax | 15% |
| Gelucire 50/13 | 5% |

The microspheres were coated at a 15% coating level with a 1:1 EC/HPC blend for taste masking.

The sachet composition contained:

| Coated aspirin microspheres | 62.6% |
|---|---|
| Citric Acid | 1.0% |
| Floss of Example II | 34.7% |
| Lemon flavor | 0.50% |
| Aspartame | 0.70% |
| Syloid | 0.50% |

Using a procedure similar to that of Example IV, the spheres and floss were screened and mixed with the other ingredients to yield a sachet product. The sachet particles were put into 650 mg doses in individual packages.

EXAMPLE VII

Using a procedure similar to that of Example VI, aspirin microspheres were made and coated.

An aspirin-containing sachet was made which included the following:

| Aspirin taste-masked spheres (70% drug) | 62.3% |
|---|---|
| Floss* | 35.1% |
| Citric acid | 1.0% |
| Lemon flavor | 0.5% |
| Cab-o-sil | 1.0% |
| Magnasweet 135 | 0.1% |

*produced using the procedure of Example III.

The aspirin microspheres and the floss were combined in a plastic bag and mixed well. Later the flavor, citric acid, Magnasweet, and Cab-o-sil were added sequentially, with mixing.

EXAMPLE VIII

Using a procedure similar to that of Example VI, aspirin microspheres were made and coated.

| The following ingredients were used to prepare a sachet | |
|---|---|
| Aspirin taste-masked spheres (70% drug) | 23.2% |
| Floss* | 75% |
| Citric acid | 0.3% |
| Lemon flavor | 0.5% |
| Cab-o-sil | 1.0% |

*produced using the procedure of Example III.

The floss was screened through a #20 mesh sieve. The citric acid was sieved through a #40 screen. A portion of the screened floss was combined with the Cab-o-sil. The aspirin microspheres were layered between the floss and mixed for 5 minutes. The citric acid and the grape flavor were added with mixing (about 3 minutes). The Cab-o-sil/floss portion was added and mixed for 2 minutes. The blend was stored.

EXAMPLE IX

The following processes were employed to produce a sachet:

A. Floss Preparation

| Ingredient | wt. % |
|---|---|
| Sucrose | 89.75 |
| Sorbitol | 10.0 |
| Polysorbate 80 | 0.25 |
| Total | 100.00 |

The ingredients were placed in an appropriate mixer and blended well. The blended mixture was put into the floss head described in U.S. Ser. No. 08/854,344, filed May 12, 1997, and processed at 60 Hz, in a temperature range of 230–250° C. The floss was placed into a Littleford FM mixer/granulator and chopped for 30 seconds. While mixing, spray ethanol (2% of floss weight) was sprayed onto the floss. The choppers were turned on for 5 seconds after 30 grams of ethanol had been added. After all of the ethanol was added, the mixer jacket was heated to 105° F. The ploughs were turned for 30 seconds every 2 minutes until the ethanol was removed.

Sachet Blend

| | wt. % | kg |
|---|---|---|
| Aspirin (70%) taste-masked microspheres | 62.3 | 93.45 |
| Floss | 35.1 | 52.65 |
| Citric Acid | 1.0 | 1.50 |
| Lemon Flavor | 0.5 | 0.750 |
| Magnasweet 135 | 0.1 | 0.150 |
| Cab-O-Sil | 0.0 | 1.50 |
| TOTAL | 100.0 | 150.0 |

The procedure used to make the sachet is: Weigh and sieve ingredients to delump. Blend ⅓ of the floss with the total amount of aspirin microspheres in a Littleford FKM600 mixer and blend at 60 Hz (134 rpm) with choppers off for five minutes. Blend another ⅓ floss with lemon flavor, then add Magnasweet 135 and blend.

Add the citric acid and the floss/lemon/magnasweet blend to the Littleford mixer containing the microspheres and floss. Set the plough speed to 60 Hz and mix the ingredients with choppers off for three minutes.

Blend the final ⅓ floss portion with the Cab-O-Sil and add it to the Littleford mixer. With the plough speed at 60 Hz, mix with choppers off for two minutes.

Package blend into sachets, based on product release assay value (theoretical 43.3% ASA) to deliver 650 mg aspirin per unit dosage.

There have been described what are presently believed to be the preferred embodiments of the invention. Those skilled in the art will realize that changes and modifications may be made thereto without departing from the spirit of the invention, and it is intended to claim all such changes and modifications as fall within the true scope of the invention.

We claim:

1. A sachet formulation containing:
   (A) coated spherical microparticles containing one or more bioaffecting agents;
   (B) partially recrystallized shearform floss particles produced from compositions containing at least one saccharide-based carrier and one sugar alcohol wherein said particles are xylitol-free; and
   (C) one or more additives selected from the group consisting of:
   lubricants, colorants, flow agents, glidants, fillers, perfumes, flavors and flavor enhancers.

2. The formulation of claim 1 wherein the particles of (B) are produced by treating amorphous floss with a crystallization modifier.

3. The formulation of claim 2 wherein the floss has been treated with about 2% to about 4% ethanol.

4. The formulation of claim 3 wherein the floss is produced from a composition consisting of sucrose, sorbitol and Polysorbate 80.

5. The formulation of claim 3 wherein the floss is produced from a composition consisting of 89.75% sucrose, 10% sorbitol, and 0.25% Polysorbate 80.

6. The formulation of claim 2 wherein the microspheres have been coated with one or more coatings to enhance taste-masking and/or release properties.

7. The formulation of claim 4 wherein the bioaffecting agent includes at least one analgesic.

8. The formulation of claim 5 wherein the bioaffecting agent is selected from the group consisting of: aspirin and acetaminophen.

9. A process for producing a sachet formulation comprising the steps:

(1) combining coated liquiflash particles with partially crystallized shearform floss particles, wherein the floss is xylitol free
(2) adding one or more additives selected from the group consisting of: lubricants, colorants, flow agents, glidants, fillers, perfumes, flavors and flavor enhancers, and
(3) mixing to produce a sachet.

10. The process of claim 9 wherein the shearform floss particles are partially crystallized by contacting them with a crystallization modifier.

11. The formulation of claim 3 wherein the floss is produced from a composition containing 74.75% sucrose, 25.0% mannitol, and 0.25% Polysorbate 80.

12. A sachet formulation produced by the process of claim 9.

13. The formulation of claim 12, wherein the floss is produced from compositions containing at least one saccharide-based carrier and one sugar alcohol and wherein said particles are xylitol-free.

14. The formulation of claim 13, wherein the floss has been treated with about 2% to about 4% ethanol.

15. The formulation of claim 14, wherein the floss is produced from a composition consisting of sucrose, sorbitol and Polysorbate 80.

16. The formulation of claim 14, wherein the floss is produced from a composition consisting of 89.75% sucrose, 10% sorbitol, and 0.25% Polysorbate 80.

17. The formulation of claim 14, wherein the microspheres have been coated with one or more coatings to enhance taste-masking and/or release properties.

18. The formulation of claim 15, wherein the bioaffecting agent includes at least one analgesic.

19. The formulation of claim 15, wherein the bioaffecting agent is selected from the group consisting of aspirin and acetaminophen.

20. The formulation of claim 14, wherein the floss is produced from a composition containing 74.25% sucrose, 25.0% mannitol, and 0.75% Polysorbate 80.

* * * * *